US009035076B2

(12) United States Patent
Benson et al.

(10) Patent No.: US 9,035,076 B2
(45) Date of Patent: *May 19, 2015

(54) RECOVERY OF LACTIC ACID VALUES FROM A MESO-LACTIDE STREAM

(71) Applicant: NatureWorks LLC, Minnetonka, MN (US)

(72) Inventors: Richard Douglas Benson, Long Lake, MN (US); Joseph D. Schroeder, Minneapolis, MN (US)

(73) Assignee: NatureWorks LLC, Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/040,530

(22) Filed: Sep. 27, 2013

(65) Prior Publication Data

US 2014/0031566 A1    Jan. 30, 2014

Related U.S. Application Data

(63) Continuation-in-part of application No. 13/203,075, filed as application No. PCT/US2010/027117 on Mar. 12, 2010, now Pat. No. 8,552,209.

(60) Provisional application No. 61/159,929, filed on Mar. 13, 2009.

(51) Int. Cl.
*C07D 319/00* (2006.01)
*C07D 319/12* (2006.01)

(52) U.S. Cl.
CPC .................................. *C07D 319/12* (2013.01)

(58) Field of Classification Search
CPC .................................................... C07D 319/12
USPC .......................................................... 549/274
See application file for complete search history.

(56) References Cited

U.S. PATENT DOCUMENTS

| 5,247,058 | A | 9/1993 | Gruber |
| 5,258,488 | A | 11/1993 | Gruber |
| 5,338,822 | A | 8/1994 | Gruber |
| 5,357,035 | A | 10/1994 | Gruber |
| 5,536,807 | A | 7/1996 | Gruber |
| 5,700,435 | A | 12/1997 | Bischof |
| 6,005,067 | A | 12/1999 | Gruber |
| 6,277,951 | B1 | 8/2001 | Gruber |
| 6,310,218 | B1 | 10/2001 | O'Brien |
| 6,326,458 | B1 | 12/2001 | Gruber |
| 8,552,209 | B2 * | 10/2013 | Benson et al. ............ 549/274 |

FOREIGN PATENT DOCUMENTS

WO           95/09879 A       4/1995

OTHER PUBLICATIONS

Tsukegi et al., in "Racemization behavior of L,L-lactide during heating", Polymer Degradation and Stability 92 (2007) 552-559.*
Tsukegi et al, "Racemization behavior of L-L-lactide during heating", Polymer Degradation and Stability 92 (2007) 552-559.
Nomura et al., "Stereoselective Ring-opening polymerization of a racemic lactide . . . ", Chem. Eur J. 2007, 13, 4433-4451.

* cited by examiner

*Primary Examiner* — Nizal Chandrakumar
(74) *Attorney, Agent, or Firm* — Gary C Cohn PLLC

(57) ABSTRACT

Lactic acid equivalents are recovered from a starting lactide stream by catalytically racemizing a portion of the lactide in the stream at a temperature of 180° C. or below. This increases the proportion of two species of lactide (i.e., at least two of S,S-, R,R- or meso-lactide) at the expense of the third species. The racemized mixture so obtained can be separated to recover some or all of one or more of the lactide species from the remaining lactide species, by a process such as melt crystallization or distillation. Impurities in the starting lactide stream usually are retained mostly in the remaining meso-lactide, so a highly purified S,S- and/or R,R-lactide stream can be produced in this manner. Such a purified S,S- and R,R-lactide stream is suitable for polymerization to form a polylactide.

15 Claims, No Drawings

RECOVERY OF LACTIC ACID VALUES FROM A MESO-LACTIDE STREAM

This application claims priority from U.S. Provisional Patent Application No. 61/159,929, filed 13 Mar. 2009.

This invention relates to methods for making lactide and poly(lactic acid) (polylactide) resins.

Lactide is a monomer that is polymerized to produce polylactide resins. Processes that are suitable for large-scale production of polymer grade lactide from lactic acid are described, for example, in U.S. Pat. Nos. 5,247,058, 5,258,488, 5,357,035, 5,338,822, 6,005,067, 6,277,951 and 6,326,458. The processes described in these patents generally involve polymerizing lactic acid to form a low molecular weight polymer, and then depolymerizing the low molecular weight polymer. The depolymerization step produces lactide. The lactide is then purified to separate it from impurities that may include, for example, water, residual lactic acid, linear lactic acid oligomers, and other impurities.

Lactic acid is a molecule with one chiral center, and so it exists as two optical isomers, the so-called R- (or D) enantiomer and the S- (or L) enantiomer. The lactic acid that is used as the raw material for producing lactide is usually of very high optical purity. As the lactic acid passes through the steps of forming the lactide, it is exposed to elevated temperatures and some of the lactic units convert from one optical isomer to another, to form a mixture of the R- and S-enantiomers. The process of converting one optical isomer of an organic compound to another is known as "racemization".

Lactide corresponds to the condensation product of two molecules of lactic acid to form a 3,6-dimethyl-1,4-dioxane-2,5-dione. Lactide therefore can be considered as being made up of two "lactic units", each of which has the formula $C_3H_4O_2$. Each lactic unit in a lactide molecule contains one chiral center and exists in either the R- or the S-form. A lactide molecule can take one of three forms: 3S,6S-3,6-dimethyl-1,4-dioxane-2,5-dione (S,S-lactide), 3R,6R-3,6-dimethyl-1,4-dioxane-2,5-dione (R,R-lactide), or 3R,6S-3,6-dimethyl-1,4-dioxane-2,5-dione (R,S-lactide or meso-lactide). These have the following structures:

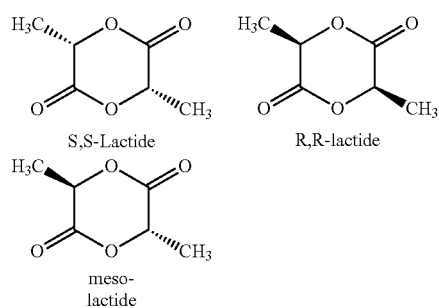

S,S-lactide and R,R-lactide are a pair of enantiomers, while meso-lactide is a diastereomer.

Most lactic acid that is produced commercially is the S-enantiomer. When S-lactic acid is converted to lactide, the major product is therefore S,S-lactide. However, because some of the S-lactic acid racemizes to R-lactic acid, some R,R-lactide and some meso-lactide are also produced. The ratios of S,S-lactide, meso-lactide and R,R-lactide that are produced when the low molecular weight polymer depolymerizes can be estimated as:

S,S-lactide mole fraction≈$(F_S)^2$
R,R-lactide mole fraction≈$(F_R)^2$
Meso-lactide mole fraction≈$2F_R F_S$ wherein $F_R$ is the mole fraction of R-lactic enantiomer and $F_S$ is the mole fraction of S-lactic enantiomer in the low molecular weight polymer which is depolymerized to form the lactide. There is a small kinetic bias towards making S,S-lactide and R,R-lactide, and so the foregoing estimates may slightly overestimate the amount of meso-lactide that is produced. The meso-lactide fraction will be larger than the R,R-lactide fraction when $F_R$ is smaller than $F_S$, as is normally the case. The R,R-lactide fraction is often quite small.

It is usually necessary to separate meso-lactide from the rest of the lactide stream. There are two reasons for this. One has to do with controlling the proportion of the R-lactic acid units in the lactide stream that is taken into the polymerization step. It is important to control the ratio of S- and R-lactic units in the lactide stream, as that ratio can significantly affect the crystalline properties of a polylactide made by polymerizing the stream. Removing meso-lactide from lactide stream has the effect of reducing the proportion of R-lactic acid units, which leads to the production of a more crystalline grade of polylactide.

The second reason has to do with removing certain impurities from the lactide. Certain common separation methods, such as distillation and melt crystallization, tend to concentrate impurities in the meso-lactide stream, thereby further purifying the S,S- and R,R-lactide stream.

The separated meso-lactide stream contains lactic acid equivalents, which are valuable if they can be recovered. However, a significant amount of clean-up is needed because impurities tend to become concentrated in that stream. It has been difficult to remove certain impurities from this stream in an economical way. Distillation methods are ineffective at a commercial scale, because at least some of the impurities have volatilities very close to that of meso-lactide. Another problem is that the meso-lactide stream is very optically impure because it contains high proportions of both S- and R-lactic acid units. It can be blended with an S,S-lactide stream in small proportions (less than about 15% by weight meso-lactide) to produce a semi-crystalline polylactide, but the meso-lactide stream only produces amorphous polylactide grades if polymerized by itself or in higher proportions. As a result of these problems, much or all of the meso-lactide is usually discarded or used in other, non-polymer applications which have lower value. These problems reduce overall yields and increase the overall cost of the process.

In cases such as just described, it would be desirable to reduce these yield losses by recovering lactic acid equivalents from the meso-lactide stream in a form that can be used to make polylactides. It is further desirable to recover those lactic acid equivalents mainly in the form of lactide, rather than in the form of lactic acid or linear lactic acid oligomers.

To state the problem more generally, there sometimes exist situations in which an available lactide stream contains a diastereomeric and/or enantiomeric composition that is different from what is needed for a particular application. The most usual case is the one just described, in which a meso-lactide stream is available and S,S-lactide and/or R,R-lactide are what is needed. However, other cases can exist. For example, an available lactide stream may contain predominantly S,S- or R—R-lactide, when a stream rich in meso-lactide is required. In another possible scenario, a predominantly S,S-stream may be available while R,R-lactide is required, or vice versa. In each of these situations, it is desired to extract as much of the wanted lactide product as possible from the available lactide stream, and so reduce yield losses.

Another desired outcome would be to obtain the desired lactide product in a somewhat purified state. As discussed more fully below, in certain manufacturing processes in which meso-lactide is separated from S,S-lactide and/or R,R-lactide, many of the impurities tend to become concentrated in the meso-lactide stream. For example, distillation and melt crystallization methods for removing meso-lactide from the other forms will preferentially leave impurities with the meso-lactide, and produce a stream of S,S-lactide and/or R,R-lactide that is relatively clean. The impurities that remain with the meso-lactide are often difficult to separate from it. It would be desirable to provide a method in which lactide values can be recovered from a meso-lactide stream that is contaminated with these impurities, and in which the recovered lactide values are relatively free of those impurities.

Although lactic acid can easily racemize, and lactide units within a lactic acid oligomer can isomerize, lactide itself is not known to racemize under any reasonable conditions. Tsukegi et al., in "Racemization behavior of L,L-lactide during heating", *Polym. Degradation and Stability* 92 (2007) 552-559, report that racemization of L,L-lactide to DD-lactide and meso-lactide can occur. However, the racemization proceeds very slowly at temperatures less than 270° C., and at those temperatures large amounts of oligomers form.

This invention is in one aspect a process for recovering lactic acid values from a starting lactide composition comprising a) subjecting a starting lactide composition to a temperature of up to 180° C. in the presence of a racemization catalyst for a time sufficient to racemize at least a portion of the lactide in the starting lactide composition to form a racemized lactide mixture that contains meso-lactide, S,S-lactide and R,R-lactide in relative proportions different than in the starting lactide composition.

The catalytic racemization permits commercially reasonable racemization rates to be achieved without producing large amounts of ring-opened species such as lactic acid or lactic acid oligomers. The process is especially useful for producing S,S- and R,R-lactide from meso-lactide, but is also useful for producing meso-lactide from S,S- and/or R,R-lactide, S,S-lactide from R,R-lactide, or R,R-lactide from S,S-lactide, if desired.

A preferred process includes the additional step b) of separating the racemized lactide mixture to obtain at least one lactide product that is enriched in S,S-lactide, R,R-lactide or meso-lactide, or any two thereof, relative to the racemized lactide mixture.

Useful racemization catalysts include a metal carboxylate salt, a metal sulfonate, sulfinate, phosphonate or phosphinate salt, or a non-nucleophilic acyclic or cyclic tertiary amine compound;

For purposes of this invention, the term "racemize" or "racemization" refers simply to a process in which one diastereomeric or enantiomeric form of lactide, i.e., S,S-lactide, R,R-lactide or meso-lactide, becomes converted to another diastereomeric or enantiomeric form of lactide. This includes the case in which meso-lactide isomerizes, at equal rates, to S,S-lactide and R,R-lactide, including in particular a process in which meso-lactide produces racemic-lactide. It further includes the conversion of S,S-lactide or R,R-lactide to meso-lactide. Those terms are not intended to mean that the isomerization is continued until a chemical equilibrium amongst all the lactide forms is reached, although in specific embodiments this occurrence may take place.

"Racemized lactide mixture" is used herein as a shorthand to denote a mixture of S,S-, R,R- and meso-lactide that is produced in step a) of the process, i.e., by racemization of a starting lactide stream. Similarly, the term "racemized S,S-lactide and R,R-lactide" is used as a shorthand to denote S,S-lactide and R,R-lactide that is produced in step a) of the process, i.e., by racemization of a starting lactide composition. The term "racemized" in this context is not intended to specify any particular properties or composition of the specified material, other than its source.

"Racemic lactide" refers to an approximately 50/50 mixture of S,S-lactic acid and R,R-lactic which has a melting temperature of approximately 127° C.

This process provides at least three main advantages. First, lactic acid equivalents from the starting lactide stream are recoverable mainly in the form of lactide (i.e., S,S-, R,R- and/or meso-lactide), rather than as lactic acid or lactic acid oligomers. Little of the starting lactide reacts to form hydrolyzed species such as lactic acid or linear lactic acid oligomers. Instead, the starting lactide is believed to racemize directly, without going through a ring-opened intermediate. The lactide product that is obtained can be sent directly to polymerization in some cases, and in other cases can be recycled into various places within a lactide production process to further purify it if needed. In either case, lactic acid equivalents are recovered from the starting lactide in the form of lactide molecules, and process losses are reduced.

The second advantage is that the amount of unwanted lactide is correspondingly reduced. Therefore, a smaller amount of lactide must be discarded or used in lower-value applications. As described below, lactide that remains after the separation step can in some cases be recycled back into one or more upstream processes.

A third main advantage is impurities tend to become concentrated in the lactide that remains after the racemization and separation step. This is especially the case when the remaining lactide is rich in meso-lactide. As a result, a lactide product obtained in step b) which is enriched in S,S- and/or R—R-lactide and depleted in meso-lactide, compared to the racemized lactide mixture, often is purified as a result of the process, by which it is meant simply that the concentration of impurities in that lactide product is less than in the starting lactide composition. A lactide product obtained from step b) of the process, which is enriched in S,S- and/or R,R-lactide but depleted in meso-lactide, compared to the racemized lactide mixture, often can be polymerized with little or no further purification to produce a polylactide resin.

In certain embodiments, the starting lactide composition is produced by separating a lactide mixture to form a meso-lactide-enriched stream and an S,S- and R,R-lactide stream that is depleted of meso-lactide relative to the meso-lactide stream. Either of these streams can be used in this process as the starting lactide composition, but the meso-lactide-enriched stream is the preferred starting lactide composition. More specifically, in certain embodiments the starting lactide composition is produced by 1) forming a low molecular weight poly(lactic acid);
2) depolymerizing the low molecular weight poly(lactic acid) to form a crude lactide; and then;
3) removing meso-lactide from the crude lactide in one or more steps such that
   A) a meso-lactide stream is formed; and
   B) an S,S- and R,R-lactide stream is formed which is depleted of meso-lactide relative to the meso-lactide stream.

In these embodiments, the meso-lactide stream produced in step 3) is taken into the racemization process of this invention.

The step of removing meso-lactide from the crude lactide in step 3) preferably is conducted by performing a fractional distillation on the crude lactide. In another approach, step 3) is conducted by melt crystallization, and the meso-lactide stream is produced as a residue stream in the melt crystallization. Other separation methods such as solvent crystallization also can be used. The step of removing meso-lactide from the crude lactide is preferably performed so that impurities in the crude lactide become concentrated in the meso-lactide stream.

In each of the foregoing aspects and specific embodiments, all or a portion of the racemized lactide product formed in step a) of the process or recovered in step b) of the process may be polymerized to form a polylactide, with or without such as the S,S- and R,R-lactide stream that is obtained when meso-lactide is separated from the crude lactide stream in step 3) above.

Because the starting lactide composition of most interest is believed to be a meso-lactide composition, the invention will be described in more detail from that perspective. The process operates in a manner completely analogous to that described in more detail below when the starting lactide composition contains mainly S,S-lactide, mainly R,R-lactide, or mainly a mixture of S,S-lactide and R,R-lactide.

Various processes for producing lactide are known, and this invention can be used in connection with any of those processes, provided that a mixture of meso-lactide and at least one of S,S-lactide and R,R-lactide is produced. Generally, these processes start with lactic acid or a derivative such as a lactic acid salt or a lactic acid ester. In a particularly useful process for producing lactide, lactic acid or a derivative is polymerized to form a low molecular weight poly(lactic acid) which is depolymerized to form lactide. Processes such as these are described in U.S. Pat. Nos. 5,536,807, 6,310,218 and WO 95/09879. These processes produce a mixture of S,S-lactide, R,R-lactide and meso-lactide.

The low molecular weight poly(lactic acid) is suitably prepared by forming a concentrated lactic acid or lactic acid derivative stream that contains from 60 to 95% by weight lactic acid or lactic acid derivative in water or, less preferably, another solvent. This stream may contain some oligomeric species that form as the concentrated stream is produced. This starting material is then further concentrated by removing water (or a lower alcohol in the case of a lactic acid ester) and solvent (if any) in an evaporator. This causes the lactic acid or derivative to condense, eliminating water or a lower alcohol as the condensation by-product. As this is an equilibrium reaction, the removal of condensation by-products favors the further condensation of the lactic acid or lactic acid derivative. A low molecular weight poly(lactic acid) formed this way has a molecular weight of up to about 5000, preferably from 400 to 3000.

The low molecular weight poly(lactic acid) is then depolymerized by subjecting it to an elevated temperature and subatmospheric pressure, typically in the presence of a depolymerization catalyst. Conditions are generally selected to (1) minimize residence time, as doing so reduces the amount of racemization that can occur prior to depolymerization, and (2) vaporize lactide that is formed. The depolymerization reaction is usually catalyzed with a tin or other metallic catalyst. Like the polymerization reaction, the depolymerization is an equilibrium reaction and removal of the lactide as it is formed favors the production of additional lactide. Therefore, continuous removal of crude lactide is preferred. The crude lactide is preferably removed as a vapor. One or more stabilizers can be present during this step as described in WO 95/09879.

The starting material used in the foregoing process is usually of very high optical purity, i.e., one enantiomer is highly predominant. As the lactic acid or derivative passes through the steps of forming the lactide, some of the lactic acid or lactic acid units in oligomerized lactic acid racemize and a mixture of S- and R-enantiomers forms.

As already described, the crude lactide that is produced as the low molecular weight poly(lactic acid) depolymerizes contains S,S-lactide, R,R-lactide and meso-lactide at ratios that are largely but not entirely statistically determined in accordance with the proportion of the S- and R-enantiomers in the low molecular weight poly(lactic acid). Of primary interest to this invention are crude lactide mixtures that contain from about 0.5 to about 30%, especially from 2 to 30% by weight meso-lactide (based on the combined weight of lactide in the mixture). The remaining lactide in those mixtures will be predominantly S,S-lactide or predominantly R,R-lactide. In the usual case, S,S-lactide will be the predominant species, and R,R-lactide will be non-predominant. To simplify the following discussion, it will be assumed that S,S-lactide is the predominant lactide species in the crude lactide. However, the invention can be practiced equally well using a crude lactide that is either predominantly S,S-lactide or predominantly R,R-lactide.

The crude lactide formed in the depolymerization step usually contains, in addition to the lactides, impurities such as residual water, some lactic acid (or a lactic acid salt or ester, if used as the starting material), some linear oligomers of lactic acid, and other reaction by-products. Meso-lactide is separated from S,S- and R,R-lactide. The crude lactide stream may undergo one or more purification steps prior to or simultaneously with this separation. For example, the crude lactide may be partially condensed to separate it from more volatile impurities. Alternatively, the crude lactide can be purified by melt crystallization methods as described in U.S. Pat. No. 6,310,218. A third approach is to distill off some or all of the impurities that are significantly more volatile than meso-lactide, such as water, residual lactic acid or lactic ester starting materials, and other small organic compounds. Such a distillation step can be performed prior to or simultaneously with a fractional distillation step in which meso-lactide is separated from the S,S- and R,R-lactide.

Meso-lactide can be separated from the S,S- and R,R-lactide by distillation, melt crystallization or other suitable processes. For economic reasons, distillation processes are preferred at large scale. The separation creates a meso-lactide stream and an S,S- and R,R-lactide stream.

The S,S- and R,R-lactide stream obtained by separating meso-lactide from the crude lactide stream contains essentially all of the S,S- and R,R-lactide that were present in the crude lactide stream, and may contain some meso-lactide. The meso-lactide composition contains mainly meso-lactide. For purposes of this invention, a meso-lactide composition is considered to contain at least 60% by weight of meso-lactide, and may contain at least 80% or at least 90% by weight of meso-lactide, based on the total weight of lactide in the composition. It may contain small quantities of S,S- or R,R-lactide, but these together generally constitute no more than about 40%, preferably no more than 20% and even more preferably no more than 10% by weight of the lactide content of a meso-lactide composition. Thus, the meso-lactide composition is enriched in meso-lactide, compared with the S,S- and R,R-lactide stream and compared with the crude lactide.

It is difficult to separate some of the impurities from lactide in a distillation process because those impurities have volatilities so similar to meso-lactide and S,S- or R,R-lactide. Process economics often dictate against making this additional separation in a distillation column, either because of the cost of the necessary equipment, the impact on operating rates, or some combination of both. Most if not all of these will remain in either the meso-lactide stream or the S,S- and R,R-lactide stream after the fractional distillation step. The impurities tend to become more concentrated in the meso-lactide stream when the meso-lactide is separated from the S,S- and R,R-lactide, especially when the separation is performed by a fractional distillation. Typically, therefore, the meso-lactide stream is enriched in impurities, relative to the crude lactide stream and the S,S- and R,R-lactide streams. The S,S- and R,R-lactide streams are greatly depleted in impurities, relative to the crude lactide stream and the meso-lactide stream.

A starting lactide composition that is taken for racemization (such as a meso-lactide composition as described above) may contain up to about 20%, more typically up to about 5% by weight, of impurities (i.e., materials other than a species of lactide). However, the starting lactide composition should contain no more than 50 milliequivalents/gram of hydroxyl-containing species, and preferably less than 20 milliequivalents/gram of hydroxyl-containing species.

A starting lactide composition, such as a meso-lactide stream produced in the manner described above (or by other appropriate process), forms the starting material that is taken into step a) of the inventive process. The starting lactide composition is racemized in the presence of a racemization catalyst and at a temperature of up to 180° C., for a time sufficient to racemize a portion of the starting lactide, so that the proportions of S,S- R,R- and meso-lactide become changed in the composition. When the starting lactide composition is a meso-lactide composition, the net effect of the racemization is to convert meso-lactide into racemized S,S-lactide and R,R-lactide. Thus, an S-lactic unit is converted to an R-lactic unit, or vice versa. When an S-lactic unit of a meso-lactide molecule racemizes, the meso-lactide molecule is converted to R,R-lactide. Similarly, when an R-lactic unit of a meso-lactide molecule racemizes, a molecule of S,S-lactide is formed.

Meso-lactide, S,S-lactide and R,R-lactide can all racemize under the conditions of the racemization reaction. A molecule of meso-lactide has a statistically equal chance of racemizing to S,S-lactide or R,R-lactide. As S,S-lactide and R,R-lactide molecules are formed, these can also racemize back to meso-lactide (which can racemize again to S,S- or R,R-lactide). Likewise, any S,S- or R,R-lactide in the starting mixture can racemize to meso-lactide. Because the racemization reactions are random (tending towards a temperature-dependent chemical equilibrium unless one or more of the lactide forms is selectively removed), the proportions of meso-lactide, S,S-lactide and R,R-lactide that are present in a racemizing mixture at any given time, assuming no removal of product, will depend on (1) the proportions of meso-, S,S- and R,R-lactide in the starting mixture, (2) the racemization temperature, (3) the type and amount of catalyst and (4) the amount of time the mixture is exposed to racemization conditions. Over time, the respective proportions of S,S-, meso- and R,R-lactide will shift towards an equilibrium, which is temperature-dependent.

The temperature of the racemization reaction has three primary effects. Racemization rates increase with increasing temperature, and therefore higher temperatures are favored when a faster reaction rate is needed or wanted. On the other hand, more reaction by-products, especially linear lactic acid oligomers, form as racemization temperatures become higher. In addition, the racemization temperature affects the equilibrium proportions of S,S-, meso- and R,R-lactide that are produced, with the equilibrium shifting towards more meso-lactide production at higher temperatures. At about 160° C., for example, a racemizing lactide mixture will in time reach an equilibrium ratio of about 36% each of S,S- and R,R-lactide, and about 28% meso-lactide. At 140° C., this equilibrium ratio is about 38% each of S,S- and R,R-lactide and 24% of meso-lactide. At 105-120° C., the equilibrium ratio is about 40-42% of each of S,S and R,R-lactide and about 15-20% of meso-lactide. Of course, more S,S- and D,D-lactide can be produced by shifting the equilibrium by removing S,S- and R,R-lactide as the racemization reaction proceeds.

Therefore, the racemization temperature should be selected in any particular case to balance these effects. The racemization temperature should be above the melting temperature of meso-lactide, which is approximately 56° C. More preferably the racemization temperature is at least 97° C. The racemization temperature is no greater than 180° C., preferably no greater than 170° C., to avoid producing significant quantities of linear lactic acid oligomers. If too many linear lactic acid oligomers are produced, they must be removed before the S,S- and R,R-lactide can be used in a polymerization reaction, which can result in a loss of yield, increased purification costs, or both.

In some embodiments, the racemization temperature is above the melting temperature (127° C.) of so-called racemic lactide, which is a 50/50 mixture of S,S- and R,R-lactide. In those embodiments, an especially preferred racemization temperature range is from about 135 to 170° C., especially about 140 to 160° C.

In other embodiments, the racemization temperature is at or below the melting temperature of racemic lactide. In those cases, a preferred racemization temperature is from 90 to 125° C., especially from 90 to 115° C. and preferably from 90 to 100° C. Under these conditions the mixture can be directed to a situation where the concentration of R,R- and S,S-lactide at the chemical equilibrium would exceed the solubility limit at the chosen temperature. Thus, as meso lactide is converted to R,R- and S,S-lactide, the R,R- and S,S-lactide can reach a concentration where they crystallize out of the solution, often in the form of racemic lactide. In this manner the meso-lactide can be converted directly to a crystallized mixture of R,R- and S,S-lactide without reaching the chemical equilibrium limit.

In still other embodiments, a portion of the racemization step can be conducted at a temperature above 127° C., such as from 135 to 170° C. or from 140 to 160° C., to take advantage of faster racemization rates. This temperature may be used, for example, until the meso-lactide content in the racemizing mixture drops below, for example, 40%, 30%, at which point the racemization temperature may be reduced to from 90 to 125° C., preferably from 90 to 115° C. or from 90 to 100° C. The lower temperature in the second step shifts the equilibrium away from meso-lactide, and also is amenable in some instances to simultaneous racemization and melt crystallization of the S,S- and R,R-lactide.

The racemization should be conducted in the substantial absence of water and other compounds that can react with lactide to form lactic acid, linear lactic acid oligomers, or other by-products. The starting lactide composition should contain no more than 50 milliequivalents/gram, preferably no more than 20 milliequivalents/gram, of water or other hydroxyl-containing species, including lactic acid and oligomers of lactic acid. These can be removed from the starting lactide composition using various processes, if necessary before conducting the racemization step.

By conducting the racemization reaction at the temperatures described above, and in the presence of at most low levels of hydroxyl-containing species as just described, the racemization reaction proceeds with little of the lactide being converted to ring-opened species such as lactic acid or lactic acid oligomers. Typically, 20% or less of the starting lactide is ring-opened during the racemization step, and it is sometimes the case that 10% or less, 5% or less, 2% or less or even 1% or less of the starting lactide is ring-opened.

A catalyst is used in the racemization step so that reaction rates are increased. Efficient catalysts include N,N'-dialkyl piperazine compounds such as those having the structure:

wherein each R is independently alkyl or aryl-substituted alkyl. The alkyl group may be linear, branched or cyclic. Examples of suitable N,N'-piperazine compounds include 1,4-dimethyl piperazine, 1,4-diethyl piperazine and the like.

Other efficient catalysts include pyridine, and substituted pyridine compounds, including those having the structure

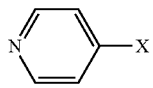

wherein X is an electron-donating group. X is preferably an —NR'R" group, wherein R' and R" are each alkyl or aryl-substituted alkyl, or R' and R" together form a divalent group that forms a ring structure that includes the nitrogen atom of the —NR'R" group. The R' and R" groups may be linear, branched, or cyclic. R' and R" are preferably each methyl or ethyl. Specific catalysts of this type include 4-dimethylaminopyridine and 4-diethylaminopyridine.

Other efficient catalysts include alkali metal salts of alkanoic acids having one to 6 carbon atoms. The alkanoic acid may be linear or branched, and may be substituted with, for example, one or more aryl groups. Example of such alkanoic acid salts include sodium acetate, potassium acetate, cesium acetate, lithium acetate, sodium, potassium, cesium and/or lithium proprionate; sodium, potassium, cesium or lithium formate; sodium, potassium, cesium or lithium butyrate, sodium, potassium, cesium or lithium 1-hexanoate, sodium, potassium, cesium or lithium benzoate, and the like.

Other efficient catalysts include alkali metal phosphates, including those having the structure

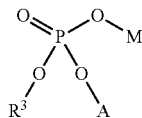

wherein M is an alkali metal, A is hydrogen or an alkali metal, and $R^3$ is hydrogen, an alkali metal or an organic group bonded to the adjacent atom through a carbon atom. When organic, $R^3$ may be a hydrocarbyl group such as aryl, aliphatic or cycloaliphatic, and may be substituted and/or branched. An aryl substituent may be further substituted with one or more aliphatic substituents. An aliphatic or cycloaliphatic substituent may be further substituted with one or more aryl substituents. M is any alkali metal and is preferably sodium or potassium. When A is an alkali metal, it is preferably sodium or potassium. Examples of alkali metal phosphates include, for example, sodium phosphate, sodium phenylphosphate, sodium dihydrogen phosphate, disodium hydrogen phosphate, potassium phosphate, potassium phenylphosphate, dipotassium hydrogen phosphate, potassium dihydrogen phosphate, and the like.

Other efficient catalysts include conjugate bases of carboxylic acids, such as metal carboxylate salts of main group and transition metals. The carboxylic acid can vary widely, its choice being based on such attributes as basicity, solubility, and thermal stability. Other useful catalysts include metal salts of Group 5A and 6A acids, including metal salts of sulfonates ($RSO_3$—), sulfinates ($RSO_2$—), phosphonates [$(RO)_2P(O)O$—] and phosphinates [$(RO)_2PO$—], wherein R in each case is hydrocarbyl, preferably alkyl. Especially preferred catalysts are homogeneous in the reaction mixture at the reaction temperature or immobilized on a solid support.

Other suitable catalysts include non-nucleophilic bases such as acyclic and cyclic tertiary amines such as triethyl amine and 1,4-diazabicyclo[2.2.2]octane, respectively. Still other useful catalysts include non-nucleophilic heterocyclics, such as pyridine and lutidine, as well as non-nucleophilic amidines such as 1,8-diazabicyclo[5.4.0]undec-7-ene. Non-nucleophilic bases in combination with Lewis acids are also useful. Examples of these include the combination bis-trimethylsilyl trifluoroacetamide and pyridine.

The catalyst should not contain reactive groups (such as active hydrogen-containing groups like hydroxyl, primary or secondary amino or thiol) that promote or engage in ring-opening reactions with the lactide. From 0.01 to about 5 parts by weight catalyst per 100 parts by weight of lactide is generally useful. A more preferred amount is from 0.1 to 2.5 parts by weight of the catalyst.

The catalyst may be affixed to a support to facilitate separation of the catalyst from the racemized lactide mixture.

As a result of the racemization, the proportions of S,S-, R,R- and meso-lactide in the lactide become changed. If the predominate lactide species in the starting lactide is S,S-lactide, then, absent any removal of material during the racemization reaction, over time the proportion of S,S-lactide will decrease and the proportions of R,R- and meso-lactide will increase. If the predominate lactide species in the starting lactide is R,R-lactide, then, absent any removal of material during the racemization reaction, over time the proportion of R,R-lactide will decrease and the proportions of S,S- and meso-lactide will increase. In the preferred case, the predominate lactide species in the starting lactide is meso-lactide, which will become less predominate over time as the proportions of S,S- and R,R-lactide increase. In all cases, the ratios of these lactide species will over time tend towards a temperature-dependent equilibrium, as discussed above, unless one or more of the lactide forms is preferentially removed.

The process preferably includes a separation step, in which at least one of the lactide species is separated from the other two species in the racemized mixture. In the preferred case, in which the starting material is a meso-lactide stream, the separation will typically include the separation of S,S-lactide, R,R-lactide or both S,S-lactide and R,R-lactide from the remaining meso-lactide.

The method by which the lactide species are separated is not critical, but the separation process preferably concentrates impurities in the remaining meso-lactide. In that manner, a racemized S,S- and/or R,R-lactide which is depleted in impurities, relative to the starting lactide composition and the remaining meso-lactide, can be removed from the product mixture.

"Depletion" in this case is with reference to the starting lactide composition; the weight ratio of impurities to the lactide content of the separated stream is lower than the weight ratio of the impurities to the lactide content of the starting lactide composition. Depletion does not require complete removal of the impurities. This relationship can be expressed by the inequality $$1 > \frac{I_{SS-RR}/(I_{SS-RR} + L_{SS-RR})}{I_{starting} \cdot (I_{starting} + L_{starting})} \quad \text{(Equation 1)}$$

where $I_{SS-RR}$ represents the weight of the impurities in the racemized S,S- and/or R,R-lactide stream separated from the reaction mixture, $L_{SS-RR}$ represents the weight of lactide in the racemized S,S- and/or R,R-lactide stream separated from the reaction mixture, $I_{starting}$ represents the weight of the impurities in the starting lactide composition and $L_{starting}$ represents the weight of lactide in the starting lactide composition. Preferably, the ratio in equation 1 is less than 0.1, more preferably less than 0.05 and even more preferably less than 0.01. An advantage of the invention is that the racemized S,S- and R,R-lactide separated from the starting lactide stream can be produced having a very low level of impurities, and so can be polymerized with little or no additional purification.

One separation method of interest is a melt crystallization method, at least in part because impurities tend to be excluded from the crystals that are formed in the crystallization step. Therefore, the melt crystallization method provides a means for simultaneously recovering lactic acid values from the starting lactide stream (in the form of S,S-lactide and/or R,R-lactide), as well as removing impurities from the recovered lactic acid values.

Melt-crystallization has previously been described as a way for purifying lactide. U.S. Pat. No. 6,310,218 describes melt crystallization as a way to concentrate an S,S-lactide-rich stream, and to produce a purified racemic lactide. In general, melt crystallization is performed on the racemized lactide stream by melting the lactide mixture, and then cooling the mixture so that the racemized S,S- and/or R,R-lactide crystallizes while leaving the bulk of the meso-lactide in the melt phase.

The melt crystallization can be conducted batch-wise or continuously. Batch methods and zone methods for conducting a melt-crystallization as described in U.S. Pat. No. 6,310, 218 are suitable. Suitable apparatus for performing industrial melt crystallizations include those described, for example, in U.S. Pat. Nos. 5,700,435, 5,338,519, 6,204,793 and 6,145, 340. In a melt crystallization method, crystals of the racemized S,S- and R,R-lactide are formed, while leaving the meso-lactide in the form of a molten liquid. The solid crystals are then separated from the molten meso-lactide.

If the racemized mixture contains nearly equal quantities of S,S-lactide and R,R-lactide, the racemized S,S-lactide and R,R-lactide can crystallize into a crystalline form known as racemic-lactide, which has a freezing temperature of about 127° C. In that circumstance, the melt crystallization can be conducted at a temperature above 56° C. (i.e., the melting temperature of meso-lactide) and below 127° C. The crystallization temperature in that case preferably is from about 100° C. to 125° C., so that crystals tend to form slowly and in that manner more completely exclude meso-lactide and impurities from their developing crystal structure.

When the racemized mixture contains significantly more S,S-lactide than R,R-lactide, or vice versa, the racemized S,S-lactide and R,R-lactide will not form a high-melting mixture. The racemized S,S-lactide and R,R-lactide instead will crystallize at or below the melting temperature of S,S- and R,R-lactide, i.e., at about 97° C. In that case, the crystallization temperature should be between 56° C. and 97° C. A preferred crystallization temperature in that case is from 80 to 95° C., to allow crystals to form slowly and in that manner more completely exclude meso-lactide and impurities from their developing crystal structure.

The racemization and melt crystallization steps can be performed simultaneously and/or sequentially. Simultaneous racemization and melt crystallization is more practical in cases in which the racemized S,S-lactide and R,R-lactide form a mixture that freezes at about 127° C. If no such mixture forms, the melt crystallization temperature must be below 97° C., at which temperature the racemization rate becomes slow. Simultaneous racemization and melt crystallization can be done, in cases in which a high-melting mixture forms, by conducting the racemization at a temperature below 127° C. A preferred temperature is from 90 to 125° C., and a more preferred temperature is from 90 to 115° C. Using this approach, the racemized R,R-lactide and S,S-lactide that forms will crystallize as racemic lactide (i.e., a high-melting mixture) as the racemization reaction proceeds. This approach has the advantages of being easily adapted to continuous operation. When the starting lactide is a meso-lactide stream, this approach has the additional advantage of continually removing R,R- and S,S-lactide from the system, thereby favoring more R,R- and S,S-lactide production, as the chemical equilibrium between the lactide forms is never reached.

In a sequential operation, the starting lactide composition is racemized first, followed by a separate step of removing some or all of at least one of the lactide species from the remaining species.

A hybrid process is possible, in which the starting lactide composition is partially racemized at a higher temperature, followed by cooling the resulting mixture to a second, lower temperature at which racemization can continue simultaneously with the crystallization of racemized S,S- and R,R-lactide. This approach combines the advantages of higher racemization rates with simultaneous racemization and separation. In such a hybrid process, the second, lower temperature preferably is from 100 to 125° C., more preferably from 105 to 110° C.

In any of the foregoing melt crystallization methods, the racemic lactide crystals or the S,S- and R,R-lactide crystals, as the case may be, are removed from the molten meso-lactide using any convenient solid-liquid separation method, such as filtering, decanting, centrifugation, plating the crystals out on a solid surface, and the like.

Another way to separate the S,S- and/or R,R-lactide from meso-lactide is by distillation. Distillation can be conducted at atmospheric or subatmospheric pressures. The racemization catalyst should be removed from the racemized mixture before the distillation step so that further racemization and formation of linear oligomers is minimized. Distillation produces a stream that is enriched in the racemized S,S- and R,R-lactide and a stream that is enriched in meso-lactide. As before, impurities tend to become concentrated in the meso-lactide stream. The racemized S,S- and R,R-lactide are therefore obtained as a stream that is depleted in impurities, as described before.

Yet another way to separate the S,S- and R,R-lactide from meso-lactide is by a solvent crystallization method. Suitable solvents include, for example, a halogenated hydrocarbon such as chloroform or 1,2-dichloroethane; an aliphatic or alicyclic ether such as diethylether or tetrahydrofuran; an aromatic hydrocarbon such as toluene; a hindered alcohol such as 2-propanol; and the like.

In certain embodiments of the invention, the starting lactide composition is a meso-lactide stream produced in an upstream step of separating a lactide mixture into the meso-lactide-enriched stream and an S,S- and R,R-lactide stream. In such a case, it is possible to perform step b) of the inventive process by recycling the racemized product from step a) into that upstream separation step (or into some other step that is farther upstream). In such a case, it becomes unnecessary to separate racemized S,S- and R,R-lactide from the remaining meso-lactide prior to conducting the recycling step, as the separation occurs in that upstream separation step.

It is also possible to preferentially separate out S,S- or R,R-lactide from the racemized lactide mixture. One way of doing this is by crystallizing the mixture from either a melt or from a solvent, in the presence of seed S,S- or R,R-lactide crystals. When seed S,S-lactide crystals are present, it is possible to preferentially crystallize S,S-lactide from the racemized lactide mixture, leaving R,R- and meso-lactide behind. Conversely, R,R-lactide can be preferentially separated by crystallizing in the presence of R,R-lactide seed crystals. The crystals in either case are enriched in S,S- or R,R-lactide, as the case may be, and depleted in the other lactide species, relative to the composition of the racemized lactide mixture. Crystallization conditions here are selected to promote slow crystal formation and growth, so that the unwanted lactide species do not rapidly crystallize together with the desired species.

The S,S- and/or R,R-lactide that is separated from the racemized lactide mixture in the foregoing manner can be further purified if desired. The racemized S,S- and/or R,R-lactide stream may contain various types of impurities, such as a certain amount of meso-lactide that becomes entrained in the material; small amounts linear lactic acid oligomers; small amounts of lactic acid that reforms during the racemization step, some residual quantity of other impurities, residual racemization catalyst, and the like. If significant amounts of any of these types of impurities are present, it may be necessary or desirable to remove them before the racemized S,S- and/or R,R-lactide is taken for polymerization. In addition, residual racemization catalyst is preferably removed from the racemized S,S- and/or R,R-lactide, particularly if it is to be taken to polymerization and/or recycled back into the lactide production system. Various purification approaches may be taken, including distillation, melt crystallization, solvent crystallization, absorption, extraction or like methods.

In one approach, the racemized S,S- and/or R,R-lactide is crystallized (if separated from the remaining meso-lactide by distillation) or recrystallized (if separated from the remaining meso-lactide by melt crystallization) one or more times. In a related approach, the racemized S,S- and/or R,R-lactide can be separated from the remaining meso-lactide, then crystallized, followed by "perfecting" the crystals by heating them to a temperature just below their melting point to selectively exclude entrained impurities from the crystal structure.

In a third approach, crystals of the racemized S,S- and/or R,R-lactide are washed or extracted with a suitable solvent to remove entrained impurities. The racemization catalyst in particular may be removed or deactivated this way, by washing with water or another deactivating agent.

In a fourth approach, the racemized S,S- and/or R,R-lactide is distilled to further purify it. If such an approach is adopted, it is often convenient to recycle the racemized S,S- and/or R,R-lactide back into an appropriate stage of the lactide production process, because the production process normally will already include one or more unit operations which are designed to remove various sorts of impurities. This embodiment of the invention is further explained through reference to the FIGURE. The FIGURE is a schematic diagram illustrating an embodiment of the process of the invention. The embodiment illustrated in the FIGURE illustrates various preferred or optional features. FIGURE is not intended to show specific engineering features or details, including the design of the various components shown. In addition, auxiliary equipment such as various valves, pumps, heating and cooling equipment, analytical, control devices and the like are not shown, but of course can be used as necessary or desirable.

In the FIGURE, lactic acid or lactic acid ester stream 5 containing water or, less preferably, another solvent, is fed into prepolymer reactor 1. The lactic acid or lactic acid ester concentration in stream 5 preferably is at least 60% by weight, and may be as high as 95% by weight, preferably as high as 90% by weight. Lactic acid may be obtained from a fermentation broth, which is preferably concentrated to within the aforementioned ranges in an upstream process step which is not shown in the FIGURE. The starting material is heated in prepolymer reactor 1 to cause the lactic acid or lactic acid ester to condense to form a prepolymer as described before. Most of the water, solvent (if any) and condensation by-products are removed from prepolymer reactor 1 separately from the prepolymer.

Prepolymer stream 6 is removed from prepolymer reactor 1 and transferred to lactide reactor 2, where it is depolymerized to form lactide. Lactide reactor 2 is essentially an evaporator, and can be of many types as described in WO 95/09879. Examples of suitable lactide reactors include, for example, forced circulation, short path or short tube, long-tube vertical, long-tube horizontal, falling film, agitated thin-film and disk evaporators. Film-generating evaporators, especially falling film and agitated falling film evaporators as described in WO 95/9879, are especially preferred. Various types of staged reactors are also suitable. Lactide reactor 2 is preferably operated at a pressure of from about 1 to about 100 mm Hg, preferably from about 2 to about 60 mm Hg. An elevated temperature, preferably from about 180 to 300° C. and more preferably from 180 to 250° C., is used.

The depolymerization reaction in lactide reactor 2 is usually catalyzed. As shown, catalyst is introduced to prepolymer stream 6 upstream of lactide reactor 2, through catalyst stream 18. It is also possible to introduce catalyst stream 18 directly into lactide reactor 2.

Crude lactide and a bottoms mixture are formed in lactide reactor 2. The bottoms mainly include high boiling materials and higher oligomers of lactic acid. The bottoms are withdrawn as a bottoms stream (not shown).

Crude lactide formed in lactide reactor 2 is withdrawn as stream 8 and transferred to distillation column 3. In the embodiment shown, the crude lactide is distilled in three stages, in first distillation column 3, second distillation 4 and third distillation column 20, respectively. It is possible in principle at least to carry out the entire distillation in a single column or only two distillation columns.

In the embodiment shown, crude lactide stream 8 is introduced into first distillation column 3, where it is separated into partially purified lactide stream 10 and an overhead stream (not shown). A bottoms stream (not illustrated) also may be withdrawn from first distillation column 3. The overhead stream contains some lactide together with most of the water and lactic acid. Partially purified lactide stream 10 contains lactide and most of the impurities that have relative volatilities of from 1.001 to 1.5 relative to S,S- or R,R-lactide when distilled from a lactide matrix ("intermediate-boiling impurities"). It is normally substantially depleted of water and lower-boiling impurities, although some may remain.

In the embodiment shown, partially purified lactide stream 10 is transferred to second distillation column 4, where lactide is separated from higher-boiling impurities such as linear lactic acid oligomers. This produces purified lactide stream 25 and a bottoms stream (not shown). Purified lactide stream 25 contains intermediate-boiling impurities as described before. Some volatiles (mainly water and lactic acid) may in addition be removed from second distillation column 4 (through a top outlet, not shown).

In the embodiment shown in FIGURE, purified lactide stream 25 is transferred to third distillation column 20, where the meso-lactide is separated from S,S- and R,R-lactide. As shown, this produces a purified S,S-lactide/R,R-lactide stream 13, which is withdrawn from near the bottom of third distillation column 20, and a meso-lactide stream 14, which is withdrawn from near the top of third distillation column 20. Meso-lactide stream 14 should contain no more than 50, and preferably no more than 20, milliequivalents/gram of hydroxyl-containing species such as water, lactic acid and lactic acid oligomers. A bottoms stream (not shown) may also be removed from third distillation column 20.

Purified S,S-lactide/R,R-lactide stream 13 is transferred to polymerization unit 23, where it is polymerized to form polylactide.

Meso-lactide stream 14 is taken to racemization unit 17, where at least a portion of the meso-lactide in stream 14 is racemized to form racemized S,S- and R,R-lactide. Racemized S,S- and R,R-lactide is removed from racemization unit 17 through line 15. The S,S- and R,R-lactide removed through line 15 and line 16 then can be recycled though any of all of lines 16A, 16B, 16C or 16D, optionally after being further purified in optional purification unit 19. Purification unit 19 can be any unit operation or unit operations such as those described above in which impurities are removed from the racemized S,S- and R,R-lactide.

If racemized S,S- and R,R-lactide stream 15 or 16 is sufficiently pure, it can be recycled through line 16A directly into polymerization unit 23, where it can be polymerized by itself to form an amorphous grade of polylactide. It is also possible to polymerize a stream containing both S,S- and R,R-lactide, such as a racemic lactide stream, to produce a semi-crystalline polymer having a crystalline melting temperature in the range of from about 145° C. to 210° C. or more, using certain salen- and homosalen-aluminum complexes, as described by Nomura et al., in "Stereoselective ring-opening polymerization of a racemic lactide by using achiral salen- and homosalen-aluminum complexes", *Chem. Eur. J.* 2007, 13, 4433-4451.

More typically, the S,S- and/or R,R-lactide will be polymerized as a blend with a S,S-lactide/R,R-lactide stream, such as the S,S-lactide/R,R-lactide stream entering polymerization unit 23 through line 13. In the usual process, the ratios of S,S-lactide/R,R-lactide in stream 13 and the racemized S,S- and R,R-lactide recycle stream 16A will be selected such that the resulting blend contains at least 90%, preferably from 92 to 99.5% by weight of one of S,S-lactide or R,R-lactide, and no more than 10%, preferably from 0.5 to 8%, by weight of the other. The lactide blend so produced can then be polymerized to produce a semi-crystalline polylactide resin.

If the racemized S,S- and R,R-lactide stream 15 or 16 still contains significant quantities of meso-lactide, but otherwise is purified enough to be polymerized, it may instead be recycled through line 16D back into third distillation column 20, in which the crude lactide entering from line 25 is separated into a meso-lactide stream 14 and S,S- and R,R-lactide stream 13. The racemization catalyst should be removed or deactivated in this case prior to recycling. The recycled racemized S,S- and R,R-lactide will then exit third distillation column through line 13, and most if not all of the meso-lactide will again be sent out through line 14 for racemization.

If racemized S,S- and R,R-lactide stream 15 or 16 contains significant quantities of other volatile impurities, it can be recycled through lines 16B and/or 16C to either or both of first distillation column 3 and second distillation column 4, to be purified together with the crude lactide that is produced in lactide reactor 2. Again, in this case, the racemization catalyst should be removed or deactivated.

The enriched meso-lactide stream (such as stream 21 in the FIGURE) that remains from the racemized mixture can be handled in various ways. It can be discarded or used in low value applications, an advantage of this invention in this case being that the mass of this stream is reduced relative to conventional processes and therefore there are fewer wasted lactic acid equivalents and lower disposal costs. Alternatively, the intermediate-boiling impurities can be removed from this stream, and the meso-lactide then can be recycled back into the lactide production process. This approach allows more of the lactic acid equivalents to be recovered. It is also possible to recycle it together with the racemized S,S- and R,R-lactide stream 15 or 16.

One method of removing intermediate-boiling impurities from meso-lactide is through an extraction and/or chemical treatment method. In general, methods of this type include (a) extraction with a solvent in which either the meso-lactide or the intermediate-boiling impurities (or some subset thereof), but not both, have a good solubility; (b) converting the meso-lactide and/or the intermediate-boiling impurities (or some subset thereof) to different chemical species which are more easily separated, and then separating the impurities or their reaction products from the meso-lactide or its reaction products, as the case may be. In the latter case, the separation may be done by a further distillation, an extraction process, a filtration process (if a solid chemical species is formed), or other separation technique, depending of course on the particular chemical species that are formed in a given case.

Succinic anhydride is often a large component of the intermediate-boiling impurities. Succinic anhydride can be separated from meso-lactide by washing the meso-lactide stream with a weakly basic aqueous phase. A suitable pH of the washing solution is in the range of from about 7.2 to about 11. This is believed to hydrolyze the succinic anhydride to form succinic acid and to neutralize the succinic acid. Some of the lactide may also be hydrolyzed to form mainly linear oligomers and possibly some lactic acid. The hydrolyzed and neutralized succinic acid is much more soluble in the aqueous phase than in the lactide phase, and will partition to the aqueous phase. The aqueous and organic phases are then separated to form a washed meso-lactide stream having a reduced level of intermediate-boiling impurities. The washed meso-lactide stream can be recycled into the prepolymer-forming step, or further upstream in the process.

If intermediate-boiling impurities are removed from the meso-lactide without hydrolyzing the meso-lactide to form linear oligomers or lactic acid, the meso-lactide can be recycled into any convenient portion of the process, including, for example, the prepolymerization step (i.e., into prepolymerization reactor 1 in the FIGURE), the depolymerization step (i.e., into lactide reactor 2 in the FIGURE), or a lactide distillation step (i.e., into first distillation column 3 and/or second distillation column 4 in the FIGURE). If necessary, the racemization catalyst may be removed or deactivated before the meso-lactide is recycled.

S,S- and/or R,R-lactide obtained from the process can be polymerized, if necessary after further purification as just described.

The following examples are provided to illustrate the invention, but are not intended to limit the scope thereof. All parts and percentages are by weight unless otherwise indicated.

EXAMPLES 1-3

Crude lactide is prepared by polymerizing S-lactic acid to form a prepolymer, and then depolymerizing the prepolymer to produce a crude lactide vapor stream. The crude lactide is then distilled in multiple steps to remove volatiles, and to produce an S,S-lactide stream (which contains a small amount of R,R-lactide) and a meso-lactide stream. The meso-lactide stream contains about 6.8 moles of meso-lactide/kilogram and about 0.2 moles of S,S-lactide/kilogram, and also contains intermediate-boiling impurities. It contains less than 50 milliequivalents/gram of hydroxyl-containing impurities. The meso-lactide stream is collected and cooled.

About 500 mL of the meso-lactide stream is melted in an oil bath. Na-ethylhexanoate catalyst is added at a 0.05% level. The mixture is heated in a stirred Parr reactor at 160° C. for 15 hours. Samples are taken periodically to measure the concentration of S,S-lactide, R,R-lactide and meso-lactide in the mixture.

As the reaction proceeds, the concentration of meso-lactide falls steadily, and S,S-lactide and R,R-lactide are produced at essentially equal rates. An equilibrium is established after about 15 hours reaction time. The equilibrium mixture contains about 36 mole percent each of S,S- and R,R-lactide, and about 28 mole percent meso-lactide. The reaction mixture contains less than 0.5% by weight of linear oligomers of lactic acid.

The reaction mixture is then cooled to a temperature of about 115-125° C. Racemic lactide crystals slowly form at this temperature to create a solid phase containing essentially all of the S,S- and R,R-lactide, and a liquid phase that contains meso-lactide, some S,S- and R,R-lactide, and essentially all of the intermediate-boiling impurities. The racemic lactide crystals contain less than 0.6% of linear oligomers of lactic acid.

When this example is repeated using a 140° C. racemization temperature, the meso-lactide takes longer to reach an equilibrium mixture, and the equilibrium mixture is weighted slightly more towards the S,S- and R,R-lactide. Linear oligomer content is slightly lower in the racemized product.

When the experiment is repeated at 180° C., the racemization rate is significantly faster, but the equilibrium is weighted slightly more towards meso-lactide, and linear oligomers form about 5% of the product.

EXAMPLE 4

56 parts by weight of a meso-lactide stream are melted and combined with 0.14 parts of 1,4-diazabicyclo[2.2.2]octane. The starting meso-lactide stream contains 98 mole percent meso-lactide, 2 mole percent S,S-lactide and less than 50 milliequivalents/gram of hydroxyl-containing impurities. The lactide/catalyst mixture is charged into a Sulzer static crystallizer, wherein it is maintained at 95° C. for 15.5 hours. During this time, the meso-lactide racemizes to form a mixture of S,S-, R,R- and meso-lactides, and a portion of the racemized-lactide forms a crystalline solid. After 15.5 hours, the remaining liquid (18 parts by weight) is removed from the crystallizer and analyzed. It is found to contain approximately equal quantities of R,R- and S,S-lactide, and 24.8 mole percent meso-lactide.

The crystallized material remaining in the static crystallizer is then heated gradually over a period of two to three hours. During this time, the crystals "sweat", i.e., release entrained material. This entrained material is captured, weighed and analyzed. 6.5 parts by weight of material is released during this "sweating" step; that material contains approximately equal quantities of R,R- and S,S-lactide and about 25 mole percent of meso-lactide.

The remaining crystals (30.1 parts by weight) contain about 43.3 parts by weight each of R,R- and S,S-lactide, and about 13.5 parts by weight of meso-lactide. These crystals are melted and transferred into the tubes of a falling film crystallizer. The lactide-containing tubes are then cooled to crystallize the lactide. As cooling continues, lactide crystals plate out on the internal surfaces of the tubes. The lactide crystals conduct heat poorly, and eventually heat transfer is slowed enough that crystal formation ceases. At that point, the remaining liquid is drained. 6.8 parts of liquid are removed. That liquid contains 45.5 mole percent meso-lactide and approximately equal quantities of R,R- and S,S-lactide. The 1,4-diazabicyclo[2.2.2]octane catalyst becomes concentrated in the remaining liquid.

The lactide crystals that remain in the lactide are "sweated" as before, and release 1.6 parts of a lactide that contains 38.5 mole percent meso-lactide and approximately equal amounts of R,R- and S,S-lactide.

About 21.6 parts of crystals remain. These contain about 5.0 mole percent meso-lactide and approximately equal amounts of R,R- and S,S-lactide, and are purified sufficiently to be used in a polymerization process. These crystals contain about 0.02 weight percent of the 1,4-diazabicyclo[2.2.2]octane catalyst.

To purify the crystals further, crystals are melted and again processed through a falling film crystallizer as before. After crystallization stops due to poor heat transfer, 5.7 parts of a liquid residue remains. This is drained; it contains about 17.9 mole percent of meso-lactide and again approximately equal quantities of R,R- and S,S-lactide. The crystals are "sweated" again, releasing 3.2 parts of a liquid. The crystals that remain after this second recrystallization are melted and recovered. Yield is 12.4 parts of a lactide mixture that contains 0.5 mole percent meso-lactide, 49.8 mole percent R,R-lactide and 49.7 mole percent S,S-lactide.

EXAMPLE 5

About 900 mL of a meso-lactide stream is melted in an oil bath. 1,4-Diazabicyclo[2.2.2] octane catalyst is added at a 0.5% level. The mixture is heated unstirred in a sealed vessel at 120° C. for 4 hours. Samples are taken periodically to measure the concentration of S,S-lactide, R,R-lactide and meso-lactide in the mixture.

As the reaction proceeds, the concentration of meso-lactide falls steadily, and S,S-lactide and R,R-lactide are produced at essentially equal rates. An equilibrium is established after 1 hour reaction time. The equilibrium mixture contains about 42 mole percent each of S,S- and R,R-lactide, and about 16 mole percent meso-lactide. The reaction mixture contains 15% by weight of linear oligomers of lactic acid.

The racemized mixture is cooled until it solidifies. The solidified lactide is dissolved in 1.2 L of toluene (approx. 1 g per mL) by heating to 75° C. in a two-neck 3 L flask. The solution is removed from the heat source and allowed to cool over night to deposit crystals. The crystallized lactide is isolated by filtration using a 600 mL glass frit. The recovered lactide, 618.3 g, is dissolved in 1.2 L of isopropanol by heating to 75° C. in a two-neck 3 L flask. The solution is removed from the heat source and allowed to cool for 5 hours to deposit crystals. The crystallized lactide is isolated by filtration using a 600 mL glass frit. The recovered lactide is dried in a vacuum oven at 40° C. overnight. The overall recovery of racemic-lactide is 60.3 percent based starting lactide. The lactide crystals contain 0.2 mole percent meso-lactide and nearly equal amounts of R,R- and S,S-lactide.

EXAMPLE 6

When Example 5 is repeated using 0.05% catalyst, the system does not reach an equilibrium mixture within 10 hours. At this point, the sample contains 44 mole percent meso-lactide, 30 mole percent S,S-lactide and 24 mole percent R,R-lactide. The reaction mixture contains 5% by weight of linear oligomers of lactic acid. The overall recovery of racemic-lactide is 56.7 percent based starting lactide. The lactide crystals contain 0.2 mole percent meso-lactide and nearly equal amounts of R,R- and S,S-lactide.

EXAMPLES 7-15

A meso-lactide composition made in the general method described in Examples 1-3, having a composition of 95.3% meso-lactide, 4.5% L-lactide and 0.1% D-lactide is subject to racemization in the presence of various catalysts as set forth in Table 1. Racemization conditions are as described with respect to Examples 1-3. Racemization temperature is 160° C. in all cases except Example 10, in which the racemization temperature is 130° C. Racemization time is as indicated in Table 1, as are the results of the racemization.

TABLE 1

| Ex. No. | Catalyst Type | Amount, wt-% | Temp, ° C. | Reaction Time, hr | Product Composition, meso/L/D lactides, wt-% |
|---|---|---|---|---|---|
| 7 | 1,4-dimethyl piperazine | 0.1 | 160 | 2 | 32.6/34.7/32.7 |
| 8 | Pyridine | 0.1 | 160 | 2 | 76.5/13.8/9.8 |
| 9 | 4-Dimethylamino-pyridine | 0.1 | 160 | 2 | 30.3/35.5/34.2 |
| 10 | 4-Dimethylamino-pyridine | 0.1 | 130 | 3 | 43.5/29.8/26.7 |
| 11 | Sodium phenyl phosphate | 0.1 | 160 | 4 | 42.3/30.2/27.5 |
| 12 | Sodium phosphate | 0.1 | 160 | 4 | 30.2/35.5/34.3 |
| 13 | Disodium hydrogen phosphate | 0.1 | 160 | 4 | 80.3/11.8/7.9 |
| 14 | Sodium acetate | 0.1 | 160 | 2 | 31.6/35.0/33.4 |
| 15 | Potassium acetate | 0.1 | 160 | 2 | 32.1/34.8/33.1 |

All of these catalysts showed effectiveness in catalyzing the racemization of the meso-lactide at moderate temperatures and low catalyst concentrations. Among the catalysts listed in Table 1, all but pyridine and disodium hydrogen phosphate resulted in near-equilibrium concentrations of the meso-, L- and D-lactide species during the reaction times reported in Table 1. Pyridine and disodium hydrogen phosphate are slower catalysts, but are effective, and would be expected to produce near-equilibrium concentrations of the lactide species given greater reaction time and/or greater catalyst concentration.

What is claimed is:

1. A process for recovering lactic acid values from a starting lactide composition, comprising
a) subjecting a starting lactide composition to a temperature of up to 170° C. in the presence of a racemization catalyst for a time sufficient to racemize at least a portion of the lactide in the starting lactide composition to form a racemized lactide mixture that contains meso-lactide, S,S-lactide and R,R-lactide in relative proportions different than in the starting lactide composition, where the racemization catalyst selected from the group consisting of an N,N'-dialkyl piperazine compound having the structure:

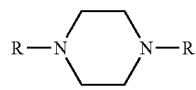

wherein each R is independently alkyl or aryl-substituted alkyl, a substituted pyridine compound having the structure

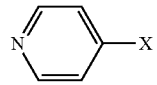

wherein X is an electron-donating group, an alkali metal salt of an alkanoic acid having one to 6 carbon atoms and an alkali metal phosphate having the structure

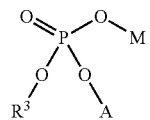

wherein M is an alkali metal, A is hydrogen or an alkali metal, and $R^3$ is hydrogen, an alkali metal or an organic group bonded to the adjacent atom through a carbon atom.

2. The process of claim 1, wherein the racemization catalyst is 1,4-dimethyl piperazine or 1,4-diethyl piperazine.

3. The process of claim 1, wherein the racemization catalyst is a substituted pyridine compound having the structure

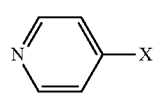

wherein X is an —NR'R" group, wherein R' and R" are each alkyl or aryl-substituted alkyl, or R' and R" together form a divalent group that forms a ring structure that includes the nitrogen atom of the —NR'R" group.

4. The process of claim 1, wherein the racemization catalyst is 4-dimethylaminopyridine or 4-diethylaminopyridine.

5. The process of claim 1, wherein the racemization catalyst is sodium acetate, potassium acetate, cesium acetate, lithium acetate, sodium, potassium, cesium and/or lithium proprionate; sodium, potassium, cesium or lithium formate; sodium, potassium, cesium or lithium butyrate, sodium, potassium, cesium or lithium 1-hexanoate, or sodium, potassium, cesium or lithium benzoate.

6. The process of claim 1, wherein the racemization catalyst is sodium phosphate, sodium phenylphosphate, sodium dihydrogen phosphate, disodium hydrogen phosphate, potassium phosphate, potassium phenylphosphate, dipotassium hydrogen phosphate, potassium dihydrogen phosphate, and the like.

7. The process of claim 1, wherein the starting lactide composition contains no more than 50 milliequivalents/gram of hydroxyl-containing compounds.

8. The process of claim 1, wherein step a) is conducted at a temperature of from 90° C. to 180° C.

9. The process of claim 8, wherein step a) is conducted at a temperature of from 135 to 170° C.

10. The process of claim 9, wherein step a) is conducted at a temperature of from 90 to 125° C.

11. The process of claim 1, further comprising b) separating the racemized lactide mixture to obtain at least one lactide product that is enriched in S,S-lactide, R,R-lactide or meso-lactide, or any two thereof, relative to the racemized lactide mixture.

12. The process of claim 11, wherein in step b), a product enriched in S,S-lactide and R,R-lactide, relative to the racemized lactide mixture, is separated from racemized lactide mixture.

13. The process of claim 12, wherein the product enriched in S,S-lactide and R,R-lactide is depleted in impurities relative to the starting lactide composition.

14. The process of claim 1 wherein step b) includes a melt crystallization step.

15. The process of claim 14, wherein the melt crystallization step is conducted at a temperature of from 90 to 125° C., and racemic lactide crystals form during the melt crystallization step.

* * * * *